United States Patent [19]

Lakatos et al.

[11] Patent Number: 5,005,146
[45] Date of Patent: Apr. 2, 1991

[54] SIGNAL PROCESSING METHOD FOR NUCLEAR SPECTROMETERS

[75] Inventors: Tamás Lakatos; József Molnár; Endre Madarász, all of Debrecen, Hungary

[73] Assignee: Magyar Tudományos Akadémia Atommag Kutató Intézete, Budapest, Hungary

[21] Appl. No.: 289,398

[22] Filed: Dec. 20, 1988

Related U.S. Application Data

[63] Continuation-in-part of Ser. No. 39,250, Apr. 16, 1987, abandoned.

[51] Int. Cl.$^5$ .............................. G06G 7/12; G01J 1/00
[52] U.S. Cl. .................................. 364/573; 364/575; 364/572; 250/336.1; 250/305
[58] Field of Search ....................... 364/573, 575, 572; 250/336.1, 305

[56] References Cited

U.S. PATENT DOCUMENTS

| | | | |
|---|---|---|---|
| 3,622,765 | 6/1969 | Anderson | 364/575 |
| 3,626,168 | 7/1969 | Norsworthy | 364/575 |
| 4,050,025 | 9/1977 | Gerber | 364/575 |

OTHER PUBLICATIONS

Markham et al., "A Pulse Height Resolution Meter", *Nuclear Instruments and Methods* 128, 1975, pp. 179-181.

*Primary Examiner*—Thomas H. Tarcza
*Assistant Examiner*—David Cain
*Attorney, Agent, or Firm*—Schweitzer Cornman & Gross

[57] ABSTRACT

The invention relates to a signal processing method and apparatus for nuclear spectrometers, whereby the peaking time is set, which is optimal from the point of view of the signal-to-noise ratio, where in case of an input signal of staircase shape modulated with noise, the so called base-line filtering interval preceeding the actual signal and the signal filtering interval following the actual signal are chosen so that their widths are equal to the width of the optimal peaking time ($T_p$), the momentary value measured in the base-line filtering interval ($A_i$) is subtracted from the momentary value measured in the signal filtering interval ($J_i$), where said momentary values ($A_i$ and $J_i$) are measured in the time scale symmetrically with regard to the rising edge of the signal, and the differences ($J_i$-$A_i$) are summed with weighting factors ($W_i$).

8 Claims, 1 Drawing Sheet

SIGNAL PROCESSING METHOD FOR NUCLEAR SPECTROMETERS

This is a continuation-in-part of U.S. Ser. No. 039,250, filed on Apr. 16, 1987 now abandoned.

BACKGROUND OF THE INVENTION

1. Field of the Invention

The present invention relates to a signal processing method and apparatus for nuclear spectrometers, by the use of which a signal processing (amplitude analyser) system of small differential non-linearity and of theoretically possible highest operating rate with optimal energy resolution can be realized, which system is independent from the input intensity.

2. Description of the Prior Art

As known, up till now solely various analogous noise filtering methods have been used for improving for energy resolution (signal-to-noise ratio) of nuclear spectrometers.

The filtered pulses are sized and divided into groups by means of so called multichannel amplitude analysers (see e.g. the instrument of type SILENA Cicero of the Italian firm Silena S.p.A). These signals are converted into digital form and stored in the appropriate channels (at memory addresses) in accordance with their values so that the memory contents are incremented.

The function of the noise filters is to improve the accuracy of the pulse amplitude measurement, as much as possible, these pulse amplitudes being proportional to the energy induced on the effect of the detected particle or quantum in the detector.

The type of the detector (ionization chamber, semiconductor detector, etc.) and the preamplifier determine the spectral distribution of the electronic noise appearing on the preamplifier output.

It has been shown that in a given system the signal-to-noise ratio can be improved only up to a certain theoretical limit by using a so called Cusp-filter. However, this filter can not be realized in the practice. The realizable and nowadays used filters are characterized by means of the so called Cusp-factor, which means the noise-to-signal ratio of the realized filter related to the Cusp-filter. This value lies between 1.016 and 1.3.

The time interval between the rising point of the signal to be measured and the moment of its measurement is known as peaking time. In case of a given type of filter, the optimal peaking time can always be found and set, with which the best signal-to-noise ratio can be achieved. The duration of this peaking time is determined by the ratio of the main noise components (series and parallel noises) of the detector preamplifier system.

The optimal peaking time varies between close limits in the cases of the known filters, their busy times, however, differ from each other in a high degree, and in accordance with this fact, their throughput rates are also different.

The reason for this fact lies in that the signal amplitudes gotten by using the known noise filtering methods are influenced even by the pulses preceeding the actual signal with a long period of time. This results in a deterioration of energy resolution, in the function of the intensity. The measure of the abovementioned deterioration may be decreased by using base-line restorers and by inserting a so called protection time.

The total busy time ($T_B$) is the sum of the peaking time ($T_P$) and the protection time ($T_{PR}$):

$$T_B = T_P + T_{PR} \tag{1}$$

In the case of the mostly used semigaussian filter $T_{PR} = 4\, T_P$, for filters having a very good Cusp-factor, the parameters of which are the function of the time, the equation $PR = 2\, T_P$ is valid.

In the case of continuous radiations (e.g. radioactive sources, continuously induced X-ray fluorescency, etc.) the time intervals between the subsequent pulses correspond to the Poisson-distribution. Supposing a semigaussian filtering, the output intensity measurable distortionfree ($R_{out}$) can be expressed in the function of the intensity to be measured (R), as follows:

$$R_{out} = R e^{-(T_B + T_P)R} \tag{2}$$

SUMMARY OF THE INVENTION

The present invention is concerned with providing a much higher signal processing rate in nuclear charged particle and photon spectrometers, by approximating the best energy resolution, as much as possible. That is, the time necessary for collecting an energy spectrum of a given accuracy is to be essentially decreased.

As it can be seen from equation (2), in case of high input intensities, the output intensity decreases exponentally, if $T_B$ is increased. Similar is the case with other types of filters.

Therefore, it is important to minimize $T_B$, which can be done by using the method the apparatus according to the invention.

Also, the present invention relates to a signal processing method for nuclear spectrometers, whereby the peaking time is set, which is optimal from the point of view of the signal-to-noise ratio; in case of an input signal of staircase shape modulated with noise, the so called base-line filtering interval preceeding the actual signal and the signal filtering interval following the actual signal are chosen so that their widths are equal to the width of the optimal peaking time ($T_P$), the momentary value measured in the base-line filtering interval ($A_i$) is subtracted from the momentary value measured in the signal filtering interval ($J_i$), where said momentary values ($A_i$ and $J_i$) are measured in the time scale symmetrically with regard to the rising edge of the signal, and the differences ($J_i - A_i$) are summed with weighting factors ($W_i$).

It is advantageous, when the momentary values are quantized.

It is further advantageous, when the results are used as channel addresses of a multichannel amplitude analyser.

It is advantageous, too, when the result is divided by the sum of the discrete values of the weighting function or by the integrate of the weighting function, respectively.

A further object of the present invention is to provide a signal processing method for nuclear spectrometers, whereby the peaking time is set, which is optimal from the point of view of the signal-to-noise ratio; in case of an input signal of staircase shape modulated with noise, the so called base-line filtering interval preceeding the actual signal and the signal filtering interval following the actual signal are chosen so that their widths are equal to the width of the optimal peaking time ($T_P$), then the sum of the weighted momentary values measured in the base-line filtering interval ($\Sigma W_i A_i$) is subtracted from the sum of the weighted momentary values measured in the signal filtering interval ($\Sigma W_i J_i$), where said momentary values ($A_i$ and $J_i$) are measured in the time scale symmetrically with regard to the rising edge of the signal.

BRIEF DESCRIPTION OF THE DRAWINGS

FIG. 2 is a block diagram of a signal processor according to the invention.

DESCRIPTION OF THE PREFERRED EMBODIMENT

Figure 1:
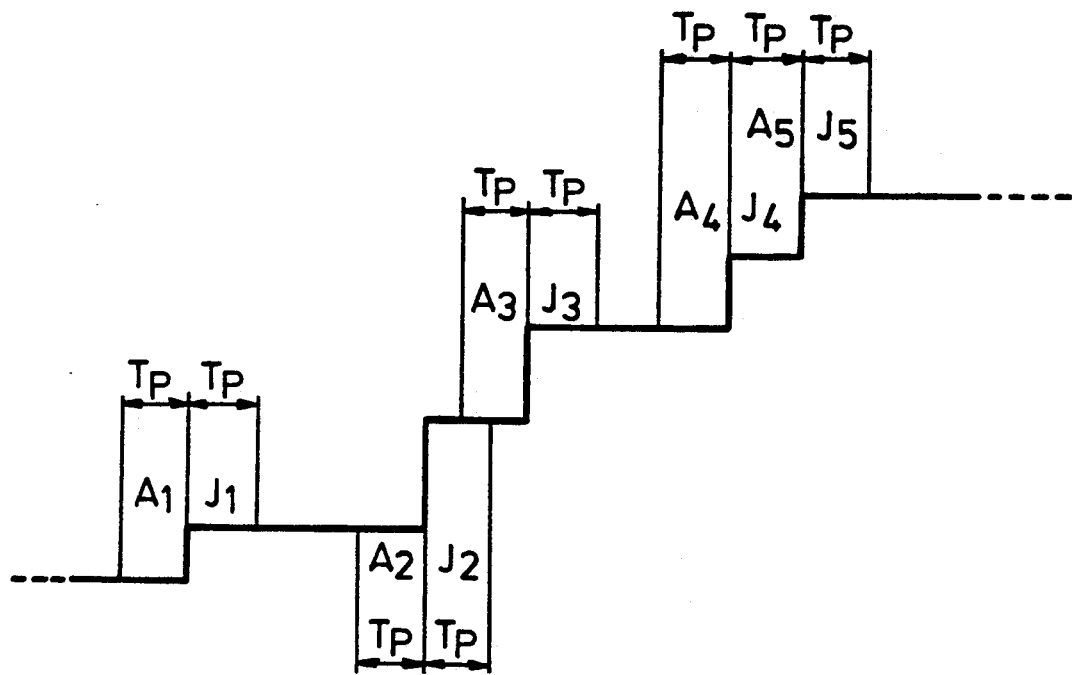
FIG. 1 is a part of the output signal series of a charge sensitive preamplifier system of a called pulsed charge restoration detector.

There is shown in FIG. 1 a part of the output signal series of a charge sensitive preamplifier system of a so called pulsed charge restoration detector, which has a staircase shape, consisting of five steps of different widths, i.e. five subsequent voltage steps with different time intervals. Let us suppose a staircase function of very wide steps (small intensity). Let us apply some kind of linear noise filtering method with parameters varying in the time or a digital noise filtering (averaging) method on the momentary values and solely on them, whereby said momentary values lie inside the time intervals of different, finite lengths preceeding and following each signal, respectively. The differences of these signals are the amplitudes of the filtered signals.

Inverting the time scale, the roles of the sections preceeding and following respectively the signal under consideration are exchanged, however, their amplitudes—disregarding the signs—remain unchanged. Taking into consideration this fact, it is easy to see that the best signal-to-noise ratio can be achieved, if the weighting functions determining the effects of the momentary values in the response function corresponding to the preceeding and the following sections, respectively, are images of each other, both sections (time intervals) having the same, and from the point-of-view of the signal-to-noise ratio optimal length. In the Figure this time interval is referred to as $T_P$, meaning the peaking time.

In the followings, it will be expedient to distinguish the time intervals $T_P$ preceeding and following the signal under consideration: the former one will be referred to as base-line filtering interval ($A_i$) the latter one as signal filtering interval ($J_i$).

In the FIG. 1 the signal filtering interval $J_2$ belonging to the second signal overlaps in a part the base-line filtering interval $A_3$ belonging to the third signal, and the signal filtering interval $J_4$ belonging to the fourth signal overlaps entirely the base-line filtering interval $A_5$ belonging to the fifth signal.

Supposing that a first filter circuit processes exclusively the "base-line", and a second filter circuit exclusively the "signals", each of the signals shown in the Figure can be measured without distortion.

In case of analogous filtering, the amplitude of the pulse can be expressed with equation (3)

$$S = K / \int_0^{T_P} W(t)J(t)dt - \int_{-T_P}^{0} W(t)A(t)dt / W(t) = W(-t) \quad (3)$$

where
W(t) is the weighting function
A(t) is the base-line signal momentary value
J(t) is the signal momentary value.

In case of digital filtering:

$$S = K \left( \sum_{i=1}^{T_P} W_i J_i - \sum_{i=-T_P}^{-1} W_i A_i \right) \quad (4)$$

where
$J_i$ and $A_i$ mean the quantized momentary values of the base-line signal and the signal, respectively.

The result will be the same, but the filtering can be realized with a simpler technic, by means of a single filter circuit, if the weighted differences of the appropriate quantized momentary values are summed:

$$S = K \sum_{i=1}^{T_P} W_i(J_i - A_{-i}) \quad (5)$$

The method according to the present invention has the advantage that no base-line stabilization is needed and the signals may succeed each other without inserting protection times. Consequently, $T_B = T_P$, that is, the busy time consists solely of the peaking time, since $T_{PR} = 0$. It can be seen that, in case of a given, preferably optimal peaking time, the method according to the present invention provides the theoretically attainable highest signal processing rate. Furthermore, the energy resolution is independent form the input intensity.

The good signal-to-noise ratio can be guaranteed with the appropriately chosen weighting function (e.g. approximation of the Cusp-method). If the factor K of equations (4) and (5) has the following form:

$$K = \frac{1}{\sum_{i=1}^{T_P} W_i} \quad (6)$$

the amplitudes of the filtered signals will be independent from the peaking time.

If in this case the peaking time ($T_{PO}$) corresponding to the optimal signal-to-noise ratio is set, but allowing the processing of signals which succeed each other in time intervals shorter that $T_{PO}$, then a signal processing can be realized without losing a number of pulses. The allowed minimum of $T_P$ can be chosen anywhere between zero and $T_{PO}$. It follows also the possibility of matching the signal processing rate and the signal-to-noise ratio to the conditions of the measurement.

When the method according to the invention is realized in digital form, the digital numbers representing the result, i.e. the amplitudes of the signals, can be used as (direct or indirect) addresses of the designated channels of a multichannel analyser. It has the advantages, among others, that no analog-to-digital converters are needed in the multichannel analysers, which are expensive, and the dead time causing by them can thereby be avoided.

One condition of the fact that the spectra can be evaluated with an appropriate accuracy, is that each channel of the analyser corresponds to equal or near equal energy intervals. The deviation of widths (channels) of these intervals are the so called differential non-linearity.

The differential non-linearity of the analog-to-digital converters used in the nuclear spectrometry should not be higher than 1%. Therefore, these converters are expensive.

The desired small differential non-linearity is guaranteed when using the method according to the present invention, on one hand by the fact that a great number of quantized samples are averaged, and on the other hand, by that the input signals fall in a random way in different ranges of the quantizing analog-to-digital converter. So an automatic averaging of the channel widths is carried out, which otherwise—in the case of the so called sliding scale method known in the nuclear electronic—would be done additionally.

The resolution (signal-to-noise ratio) in amplitude measurements on pulse signals from nuclear detectors with respect to noise and high rate effects is determined by the weighting function (W(t)) of the signal processing system. V. Radeka, Proc. Int. Symp. on Nuclear Electronics Versailles, 10–13. September 1968. p. 61-1.

The amplitude of the output signal appears as a sum of weighted samples (W(t)J(t)) at a given time (at the peaking time practically):

$$S = K \int_{-\infty}^{T_p} W(t)J(t)dt$$

All the known noise filter systems used in the nuclear spectrometric measurement are different technical realisations of the above process with different weighting functions.

In the case of the invention, one can realize a unique system with a weighting function which is symmetrical with respect to the time of the pulse appearance providing simultaneously high resolution and a much higher throughput rate then the traditional systems give.

The block diagram of FIG. 2 is a digital realisation of the invention according to equations (5) and (6).

The analogue input signal from the detector-preamplifier system (FIG. 1) is quantized by the high resolution Fast ADC 1 (Analog to Digital Converter). (The resolution must be at least 12 bits and the quantizing frequency must be higher than 5 MHz). The digital words from the ADC 1 following each other are stored in the Ring Memory 2. The Ring Memory 2 is based on a random access (RAM) memory. The word length of the memory is the same (or higher) as that of the Fast ADC resolution.

The number of the words stored in the memory 2 at a given time is determined by the required maximum peaking time divided by the clock frequency. A clock is a part of the Control Unit 3. The value of the maximum peaking time depends on the field of application. In the case of semiconductor X-ray detectors this value is between 50–200 μS, and in the case of gamma-ray detectors is between 20–50 μS. The addresses of the memory 2 are determined by Up/Down Addresses Counter 4 which is controlled by the Control Unit 3. If the memory 2 is full, a new word overwrites the oldest one. Therefore the "old" words are continuously overwriting by the new ones.

The Signal Recognition circuit 5 separates the true detector pulses from the noise events. If a pulse appears and it is detected by the Signal Recognition circuit 5, the Control Unit 3 presets the Peaking Time Preset Counter 6 and clears the output buffer of the weighted sum adder (ΣWi (Ji-A-i)) 7 and the output buffer of the weight adder (ΣWi) 8. Then the series of the weighted differences from arithmetic unit 10 are summed by the weighted sum adder 7, and the weights are independently summed in the weight adder 8 during the shaping time. The i-th weighted difference from arithmatic unit 16 appears as the difference of the i-th digital word from the Fast ADC (Ji) and the -i-th digital word from the Ring Memory (A-i) multiplied by the i-th weight (Wi) from the Weight Decoder 9. In other words Ji is the i-th sample after and Ai- is the -i-th sample before the pulse arrival. The words read from the memory 2 are selected by the Up-Down Addresses Counter 4, which selects the addresses for writing the new words too. Different solutions can be realized to point out the writing and reading addresses. One possible way is by using two counters and a multiplexer in the Up/Down Address Counter Unit 4. The first counter selects the writing addresses and always counts in the same direction (up for example). If a pulse is detected one can preset the second counter using the counts of the first one. After that the first counter continues its work, and the second counts in an opposite direction (down) selecting the addresses of the samples taken before the pulse arrival. In this case the addresses of the Ring Memory 2 for writing and for reading can be selected by multiplexing the outputs of the two counters.

The choice of the value of the different weights (weighting function) determines the resolution (signal-to-noise ratio) of the system. Different solutions are possible. The simples way is to generate a constant weighting function with value one (Wi=1). In this case instead of Wi(Ji-A-i) values we need only the Ji-A-i which can be easily done. The resolution will be better than the case of the widely used time-invariant systems. Using the above solution Weight Decoder 9 is not needed. If the weighting function is not constant, the Weight Decoder and a fast digital multiplier or multiplexor are necessary to generate the Wi(Ji-a-i) values.

The modes of operation (adaptive/non-adaptive) and the peaking time are selected by the user as microcomputer commands sent to the Control Unit through interface 14. In non-adaptive mode at the end of the peaking time interval the Peaking time Preset counter gives a ready signal to the divider unit 11, and the former generates the output value, $$S = \frac{\sum_{i=1}^{T_p} Wi(Ji - A \, i)}{\sum_{i=1}^{T_p} Wi}$$

where $T_P$ is the number of samples according to the peaking time. If a second pulse appears during the set peaking time, both pulses are rejected, that is, no output response generated. In an adaptive mode of operation is a second pulse is detected in the peaking time interval, a ready signal is immediately sent to the divider under the influence of the Control Unit 3. The output value in this case is $$Sa = \frac{\sum_{i=1}^{n} Wi(Ji - A - i)}{\sum_{i=1}^{n} Wi}$$

The sample number (n) is lower than the ideal one ($T_P$), but the S and Sa values are equal (not seeing the influence of the noise). Therefore all of the input pulses can generate an undistorted output response.

All of the systems used up to now are unadaptable. That means that in the above case they reject both pulses or give one output pulse with a distorted amplitude.

If the output value is ready, the DMA Increment Interface 12 (Direct Memory Access) connected to the microcomputer 13 increments the relevant memory byte belonging to the above output value.

In such way a part of the micro Computer memory serves as a Multichannel Analyzer Memory in which the spectra is accumulating during the measuring time. (No separate multichannel analyzer (MCA) needed. No MCA dead time appears.) The display and the evaluation of the spectra is only a question of adequate software.

What we claim is:

1. A signal processing method for nuclear spectrometers and the like adapted to analyze a series of randomly-occurring electrical data signals of random length and having randomly varying amplitudes, impressed upon electrical noise-bearing background, comprising: selecting a processing time interval for the signal, said processing time interval embracing the onset time of said signal; setting a base-line filtering time interval immediately preceding said signal onset and a signal filtering time interval immediately following said signal onset, the total duration of said intervals being equal to said processing time; continuously measuring the instantaneous voltage value in said base-line and signal filtering intervals and subtracting the base-line filtering interval voltage value from the corresponding signal filtering (internal) interval voltage to create a series of difference values, wherein said corresponding instantaneous base-line filtering interval voltage and signal filtering interval voltage values are symmetric in time offset from said onset of said signal; and summing said difference values according to a selected weighting function whereby a portion of said signal filtering interval may be used as portion of the base-line filtering interval for a following signal.

2. A signal processing method as claimed in claim 1, wherein the instantaneous voltage values are quantized and the weighting function has discrete values.

3. A signal processing method as claimed in claim 2, wherein the weighted sum of said difference values is used to define channel addresses for a multi-channel analyzer wherein the signal data is to be stored.

4. A signal processing method as claimed in claim 3, wherein the weighted sum of difference values is divided by the actual sum of the discrete values of said weighting function, and wherein when the processing of a data signal has a processing time interval selected therefor of a shorter duration than the processing time interval of the immediately-previous data signal, the processing time interval of said immediately-previous data signal is reset to be equal to said shorter processing time interval.

5. A signal processing method as claimed in claim 1, wherein said weighted sum of difference values is divided by the integral of the weighting function calculated over the length of the processing time interval; the processing of a data signal having a shorter processing time interval than the processing time interval of the immediately previously processed signal causing the processing time interval for said immediately previously processed signal to be reset to be equal to said shorter processing time interval.

6. A signal processor comprising: means for quantizing over time an analog input signal comprising an information pulse and noise components into a series of output digital words corresponding to the quantized magnitude thereof; means for storing said digital words; means for locating the leading edge of said pulse component among said digital words; means for selecting a pair of equal time intervals, the first of said intervals ending at the onset time of said pulse leading edge and the second of said intervals commencing at the onset time of said pulse leading edge; means for subtracting the values of said stored digital words corresponding to signal magnitudes at equal times prior to and after said onset time over the length of said time intervals to create a series of difference values; and means for storing said difference values.

7. The signal processor according to claim 6 further comprising means for multiplying said series of digital difference values by a weighting function on a function element-by element basis; means for summing the output of said multiplying means; means for summing the values of the elements of said weighting function; and means for diving the summed output of said multiplying means by the sum of said weighting function elements.

8. The signal processor according to claim 6, wherein the storing means comprises a ring counter memory.

* * * * *